United States Patent

Blatcher et al.

[11] Patent Number: 5,659,040
[45] Date of Patent: Aug. 19, 1997

[54] PROCESS FOR THE PREPARATION OF N-METHYL-3-(1-METHYL-4-PIPERIDINYL)-1H-INDOLE-5-ETHANESULPHONAMIDE

[75] Inventors: Philip Blatcher; Malcolm Carter, both of Stevenage; Roy Hornby, Buntingford; Martin Richard Owen, Stevenage, all of Great Britain

[73] Assignee: Glaxo Group Limited, London, England

[21] Appl. No.: 600,932

[22] PCT Filed: Sep. 27, 1994

[86] PCT No.: PCT/EP94/03216

§ 371 Date: Feb. 29, 1996

§ 102(e) Date: Feb. 29, 1996

[87] PCT Pub. No.: WO95/09166

PCT Pub. Date: Apr. 6, 1995

[30] Foreign Application Priority Data

Sep. 29, 1993 [GB] United Kingdom ............... 9320115

[51] Int. Cl.$^6$ .................................................. C07D 211/02
[52] U.S. Cl. ........................ 546/185; 546/201; 546/277.4
[58] Field of Search ......................... 546/185, 201, 546/277.4

[56] References Cited

FOREIGN PATENT DOCUMENTS

| A-0 303 507 | 2/1989 | European Pat. Off. . |
| A-0 303 506 | 2/1989 | European Pat. Off. . |
| A-0 354 777 | 2/1990 | European Pat. Off. . |
| A-0 382 570 | 8/1990 | European Pat. Off. . |

OTHER PUBLICATIONS

Hawley's, *Condensed Chemical Dictionary*, Richard J. Lewis ed., Twelfth Edition, pp. 867–868, 1993.

Primary Examiner—Matthew V. Grumbling
Assistant Examiner—Michael Bucknum
Attorney, Agent, or Firm—Bacon & Thomas

[57] ABSTRACT

A process for the preparation of the compound of formula (I)

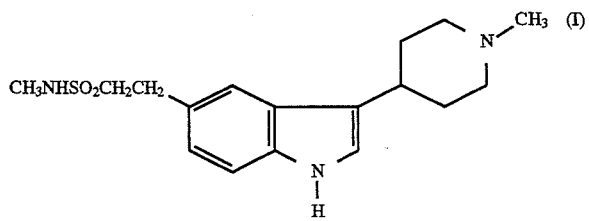

or a salt thereof which comprises reducing the compound of formula (II)

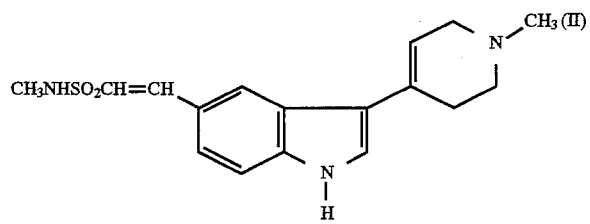

or a salt thereof.

The novel intermediate of formula (II) and processes for preparing it are also described.

16 Claims, No Drawings

PROCESS FOR THE PREPARATION OF N-METHYL-3-(1-METHYL-4-PIPERIDINYL)-1H-INDOLE-5-ETHANESULPHONAMIDE

This invention relates to a process for the preparation of N-methyl-3-(1-methyl-4-piperidinyl)-1H-indole-5-ethanesulphonamide and physiologically acceptable salts and solvates thereof.

N-Methyl-3-(1-methyl-4-piperidinyl)-1H-indole-5-ethanesulphonamide, which may be represented by the formula (I)

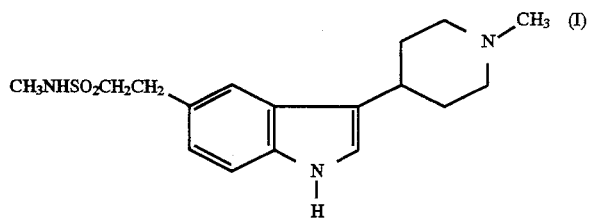

and its physiologically acceptable salts and solvates are disclosed in GB2208646. It exhibits selective vasoconstrictor activity and is indicated for use in the treatment of migraine.

GB2208646 describes inter alia a process for preparing the compounds disclosed therein which comprises reducing the appropriate 3-(1,2,3,6-tetrahydro-1-methyl-4-pyridinyl)-indole-5-ethanesulphonamide derivative and a process which comprises reducing the appropriate 3-(1-methyl-4-piperidinyl)-indole-5-ethenesulphonamide derivative. However, there is no specific disclosure of a process which comprises reducing a 3-(1,2,3,6-tetrahydro-1-methyl-4-pyridinyl)-indole-5-ethenesulphonamide derivative.

We have now surprisingly found that the compound of formula (I) can be prepared in good yield and high purity by reduction of a novel diene intermediate.

Thus, the present invention provides a process for preparing compound (I) or a salt thereof which comprises reducing the compound of formula (II)

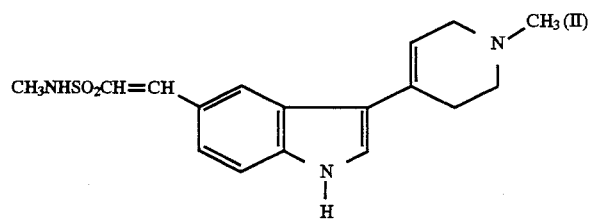

or a salt thereof.

The reduction process may conveniently be carried out in the presence of hydrogen and a noble metal catalyst such as palladium, palladium oxide, Raney nickel, platinum, platinum oxide or rhodium which may be supported, for example, on charcoal e.g. 10% palladium oxide on charcoal. Alternatively a homogenous catalyst such as tris (triphenylphosphine) rhodium chloride may be used. The reduction may be carried out in a suitable solvent or combination of solvents such as water, alcohol e.g. methanol or ethanol, ether e.g. dioxan, ester e.g. ethyl acetate or amide e.g. dimethylformamide, conveniently at a temperature of 10° to 50° C. Alternatively, the reduction may be carried out under conditions for catalytic hydrogen transfer using, for example, palladium in the presence of a hydrogen donor such as formic acid or its salts.

In a particularly preferred embodiment of the invention the reduction process is catalysed by 10% palladium oxide on charcoal advantageously added to the reaction vessel in the form of a wet paste e.g. 50% (w/w).

The intermediate of formula (II) and salts thereof are novel compounds and represent a further aspect of the invention.

Accordingly the invention provides N-methyl-2-[3-(1,2,3,6-tetrahydro-1-methyl-4-pyridinyl)-1H-indol-5-yl] ethenesulphonamide and salts thereof for use as intermediates.

Suitable salts include acid addition salts formed with organic or inorganic acids, for example hydrochlorides, hydrobromides, sulphates, phosphates, fumarates, maleates, creatine sulphates and methanesulphonates.

The compound of formula (II) or a protected derivative or a salt thereof may be prepared by condensing a compound of formula (III)

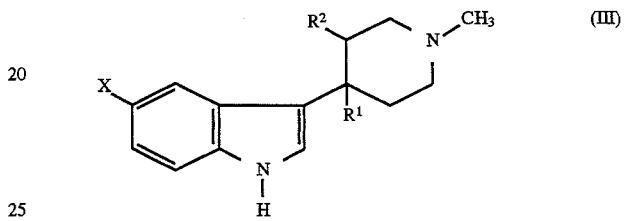

or a salt thereof, wherein $R^1$ is a hydroxy group and $R^2$ is hydrogen or $R^1$ and $R^2$ together form a double bond, X represents a leaving atom such as a halogen atom, for example a bromine atom, or a leaving group, for example a triflate ($CF_3SO_3$) group, with an N-methyl vinylsulphonamide of formula (IV)

$$CH_2=CHSO_2NZCH_3 \qquad (IV)$$

where Z is hydrogen or an amino protecting group, and optionally, if necessary and/or desired, deprotecting a protected derivative so obtained.

Typical amino protecting groups are well known to those skilled in the art and may be used in conventional manner. See, for example, "Protective Groups in Organic Chemistry", Ed. J. F. W. McOmie (Plenum Press 1973) or "Protective Groups in Organic Synthesis" by T. W. Greene (John Wiley & Sons 1981). Thus, for example, amino protecting groups include tertiary butyl, silyl, for example trimethylsilyl, aralkyl groups and acyl groups. Removal of such groups may be achieved by conventional procedures.

The reaction will generally be effected in the presence of a palladium Catalyst such as, for example palladium or palladium oxide on charcoal or a palladium salt or complex. Palladium salts which may be employed as catalysts include salts of organic adds such as acetates or salts of inorganic acids such as chlorides or bromides. Palladium complexes include, for example, lithium tetrachloropalladate and zero valent complexes such as bis(dibenzylidene-acetone) palladium and tetrakis(triphenylphosphine)palladium. Palladium acetate is a preferred catalyst.

Optionally, the reaction may be effected in the presence of a base, for example, a tertiary nitrogen base such as triethylamine or tri-n-butylamine, alkali metal carbonate such as sodium carbonate, alkali metal hydrogen carbonate such as sodium hydrogen carbonate, or an alkali metal acetate such as potassium acetate, optionally together with a phase transfer catalyst such as tetrabutylammonium chloride.

The reaction may optionally be carried out in the presence of a phosphine, for example a triarylphosphine such as triphenylphosphine or tri-o-tolylphosphine or a phosphinated polystyrene or bidentate ligand such as diphenylphosphine —(CH$_2$)$_x$-diphenylphosphine where x is an integer of 2,3 or 4. A phosphine should be present when the process is effected with a compound of formula (III) wherein X represents a bromine atom.

The reaction may be effected in the presence or absence of solvent. An anhydrous or aqueous medium comprising one or more solvents may be employed. Suitable solvents include nitriles, for example acetonitrile, alcohols, for example methanol, amides, for example dimethylformamide or dimethylacetamide, 1-methyl-2-pyrrolidinone or hexamethylphosphoramide, or water. The reaction may conveniently be carried out at a temperature of 25° to 200° C., preferably 75° to 150° C., for example 80° to 110° C.

Certain compounds of formula (III) are known and their preparation is described in GB2208646.

Thus, for example compounds of formula (III) may be prepared by condensing a compound of formula (V)

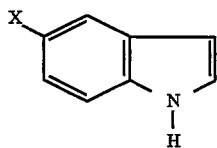

(V)

with the piperidone of formula (VI)

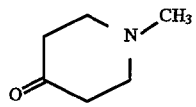

(VI)

in a suitable reaction medium in the presence of an acid or a base, conveniently at a temperature of 0° to 120° C. Compounds of formula (III) wherein R$^1$ and R$^2$ together form a double bond are preferably prepared in the presence of a base such as potassium hydroxide at an elevated temperature, for example at the reflux temperature of the reaction mixture. In contrast, compounds of formula (III) wherein R$^1$ is a hydroxy group and R$^2$ is hydrogen are preferably prepared in the presence of a base such as potassium hydroxide at room temperature. The reaction may conveniently be carried out in a suitable solvent such as an alcohol, for example methanol or ethanol. Alternatively the compound of formula (II) may be prepared by methylating the compound of formula (VII)

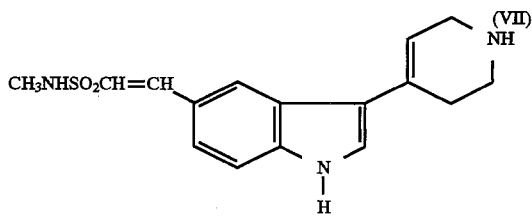

(VII)

using conventional techniques.

Thus, for example, the compound of formula (II) may be prepared by methylating the compound of formula (VII) by reductive amination using aqueous formaldehyde and sodium borohydride in a suitable solvent such as methanol or using aqueous formaldehyde and formic acid at 100° C. (Eschweiler-Clarke conditions).

Alternatively, the reaction may be effected using a suitable methylating agent such as a methyl halide, methyl tosylate or dimethylsulphate. The methylation may conveniently be carried out in an inert organic solvent such as an amide, for example dimethylformamide, an ether, for example tetrahydrofuran, an alcohol, for example methanol or industrial methylated spirits, or a nitrile, for example acetonitrile, preferably in the presence of a base. Suitable bases include, for example, alkali metal carbonates such as sodium carbonate, or alkali metal hydrogen carbonates such as sodium or potassium hydrogen carbonate. The methylation reaction is conveniently carried out at a temperature of 25° to 100° C.

The compound of formula (VII) may be prepared by reaction of the compound of formula (VIII)

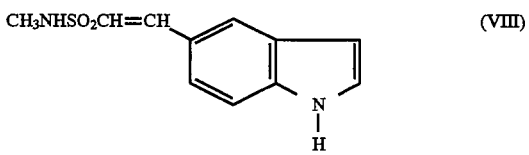

(VIII)

with the compound of formula (IX)

(IX)

using appropriate conditions as described above for the preparation of compounds of formula (III) from compounds of formula (V) and (VI).

Alternatively, the compound of formula (II) may be prepared by condensing a compound of formula (X)

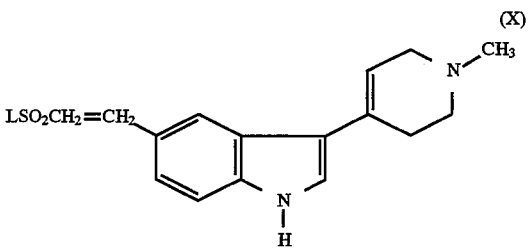

(X)

wherein L is a suitable leaving group, with methylamine. Suitable leaving groups include, for example, halogen atoms such as chlorine and aryloxy groups such as phenoxy.

The condensation process may be effected in a suitable reaction medium such as an amide e.g. dimethylformamide, an ether e.g. tetrahydrofuran, a nitrile e.g. acetonitrile, a haloalkane e.g. dichloromethane, or mixtures thereof, optionally in the presence of an organic base such as pyridine or triethylamine or an inorganic base such as calcium carbonate or sodium bicarbonate. Conveniently the reaction is effected at a temperature of −70° to 150° C.

Compounds of formula (X) may be prepared by reaction of a compound of formula (III) wherein R$^1$ and R$^2$ together form a double bond with a compound of formula (XI)

CH$_2$=CHSO$_2$Y    (XI)

wherein Y is a leaving group L as defined above or a group susceptible to replacement by a leaving group L, for example a hydroxy group, using appropriate conditions as described above for the preparation of the compound of formula (II) from compounds of formula (III) and (IV).

Thus, for example, a compound of formula (X) may be prepared by reaction of a compound of formula (III) wherein R$^1$ and R$^2$ together form a double bond with a compound of formula (XI) wherein Y is a hydroxy group, followed by reaction with a halogenating agent such as PCl$_5$ or SOCl$_2$ using conventional techniques.

Alternatively, the compound of formula (II) may be prepared by dehydrating the compound of formula (XII)

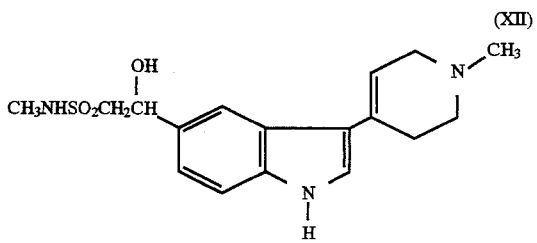

in the presence of an acid or a base.

The compound of formula (XII) may be prepared by reaction of the compound of formula (XIII)

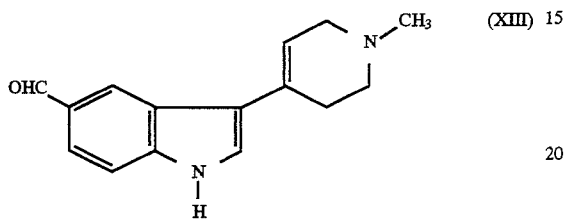

with the compound of formula (XIV)

$$CH_3SO_2NHCH_3 \qquad (XIV)$$

in the presence of a strong base such as n-butyl lithium.

The compound of formula (XIII) may be prepared by reaction of a compound of formula (III) wherein $R^1$ and $R^2$ together form a double bond with the compound of formula (XV)

$$HCON(CH_3)_2 \qquad (XV)$$

in the presence of an alkyl lithium reagent.

Alternatively the compound of formula (II) may be prepared by reacting the compound of formula (VIII) with the compound of formula (VI) using appropriate conditions as described above for the preparation of compounds of formula (III) from compounds of formula (V) and (VI).

Alternatively the compound of formula (II) may be prepared by dehydrating the compound of formula (XVI)

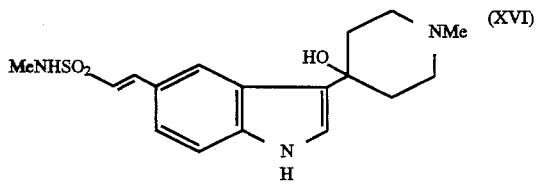

for example in the presence of an acid or a base such as potassium hydroxide.

The compound of formula (XVI) may be prepared by reaction of the compound of formula (VIII) with the compound of formula (VI) using appropriate conditions as described above for the preparation of compounds of formula (III) wherein $R^1$ is a hydroxy group and $R^2$ is hydrogen from compounds of formula (V) and (VI).

Where it is desired to isolate compound (I) as a physiologically acceptable salt, this may be formed by conventional methods, for example by treatment with an appropriate acid in a suitable solvent. Solvates of compound (I) may conveniently be prepared by crystallisation or recrystallisation from an appropriate solvent.

The invention is further illustrated by the following non-limiting examples. All temperatures are in °C. IMS means industrial methylated spirit. DMF means N-N-dimethylformamide.

Intermediate 1

5-Bromo-3-(1,2,3,6-tetrahydro-1-methyl-4-pyridinyl)-1H-indole

Process A

A mixture of 5-bromoindole (1 kg), 1-methyl-4-piperidone (692 mL) and potassium hydroxide (30.6 g) in IMS (6.0 L) was heated under reflux under nitrogen for 18 hr. The suspension was cooled to 5°–10°, aged for 15 min and filtered. The filter cake was washed with methanol (300 mL) followed by water (800 mL) then dried in vacuo at 50°. The product was obtained as a white solid (1.40 kg, 94% of theory).

NMR:—2.31 δ (3H) s; 2.54 δ (2H+DMSO-d$_5$) m; 2.61 δ (2H) m; 3.08 δ (2H) m; 6.12 δ (1H) m; 7.27 δ (1H) d of d, J=8.5 Hz, 1.9 Hz; 7.40 δ (1H) d, J=8.5 Hz; 7.50 δ (1H) s; 7.98 δ (1H) d, J=1.9 Hz; 11.4 δ (1H) broad s.

Process B

A mixture of 5-bromoindole (5.0 g), 4-dihydroxy-1-methylpiperidine hydrochloride (5.72 g) and potassium hydroxide (2.28 g) in 1-propanol (45 mL) was heated under reflux under nitrogen for 5 h. The suspension was cooled to ambient temperature and filtered. The filter cake was washed with 1-propanol (2×5 mL) followed by water (2×10 mL) then dried in vacuo at 50° overnight. The product was obtained as a white solid (5.7 g, 76% of theory).

NMR:—2.32 δ (3H) s; 2.54 δ (2H+DMSO-d$_5$) m; 2.61 δ (2H) m; 3.08 δ (2H) m; 6.11 δ (1H) m; 7.27 δ (1H) d of d, J=8.5 Hz, 1.9 Hz; 7.40 δ (1H) d, J=8.5 Hz; 7.49 δ (1H) s; 7.96 δ (1H) d, J=1.9 Hz; 11.4 δ (1H) broad s.

Intermediate 2

5-Bromo-3-(4-hydroxy-1-methyl-4-piperidinyl)-1H-indole

A mixture of 5-bromoindole (490 g), 1-methyl-4-piperidone (339 mL) and potassium hydroxide (15 g) in IMS (3 L) was stirred under nitrogen at room temperature for 24 hrs. The mixture was cooled to 7° and filtered. The filter cake was washed with ethanol (300 mL) followed by water (800 mL) to give an off-white powder which was dried in vacuo at 50° for 24 hr (563.8 g, 73% of theory).

NMR:—1.89 δ (2H) m; 2.03 δ (2H) m; 2.24 δ (3H) s; 2.55 δ (obscured by DMSO-d$_5$) m; 4.70 δ (1H) s; 7.19 δ (1H) d of d, J=8.7 Hz, 2.0 Hz; 7.24 δ (1H) d, J=2.3 Hz; 7.35 δ (1H) d, J=8.7 Hz; 7.98 δ (1H) d, J=2.0 Hz; 11.08 δ (1H) broad s.

Intermediate 3

(E)-N-Methyl-2-(1H-indol-5-yl) ethenesulphonamide.

A mixture of N-methylethenesulphonamide (45 g), 5-bromoindole (60 g), palladium acetate (0.9 g), tri-o-tolylphosphine (18.6 g) and triethylamine (90 mL) in isopropanol (300 mL) was heated at 85° under nitrogen for 18 h. The reaction mixture was cooled to ambient temperature, filtered and the filter-cake washed with isopropanol (30 mL). The combined washings and filtrate were concentrated in vacuo to give a yellow-brown solid (160 g). This material was purified by column chromatography on silica gel. Eluting initially with ethyl acetate/cyclohexane (1:1) followed by ethyl acetate provided the product (26.4 g, 36% of theory) as a yellow powder.

NMR:—2.55 δ (3H) d, J=4.9 Hz; 6.51 δ (1H) m; 6.97 δ (1H) d, J=15.5 Hz; 7.00 δ (1H) m; 7.43 δ (1H) d, J=15.5 Hz; 7.42 δ (1H) d, J=2.8 Hz; 7.45 δ (1H) d, J=8.6Hz; 7.49 δ (1H) d of d, J=8.6, 1.5 Hz; 7.90 δ (1H) s; 11.35 δ (1H) broad s.

Intermediate 4

(E)-N-Methyl-2-[3-(4-hydroxy-1-methyl-4-piperidinyl)-1H-indol-5-yl]ethenesulphonamide A mixture of (E)-N-methyl-2-(1H-indole-5-yl) ethenesulphonamide (2.0 g), 1-methyl-4-piperidone (1.62 g) and potassium hydroxide (0.7 g) in IMS (20 mL) was stirred at ambient temperature for 22 hr. The reaction mixture was concentrated and the residue purified by column chromatography on silica gel. Eluting with dichloromethane/ ethanol/ammonia (25:10:1) gave an oil which solidified on standing to a brown solid. Trituration with ether provided the product as a white powder (1.85 g, 64% of theory).

NMR:—1.94 δ (2H) m; 2.10 δ (2H) m; 2.24 δ (3H) s; 2.46 δ (2H) m; 2.55 δ (2H+DMSO-$d_5$) m; 4.69 δ (1H) broad s; 6.93 δ (1H) d, J=15.4 Hz; 7.00 δ (1H) broad s; 7.25 δ (1H) d, J=1.7 Hz; 7.42 δ (1H) d, J=8.5 Hz; 7.45 δ (1H) d, J=15.4 Hz; 7.49 δ (1H) d of d, J=8.5,1.7 Hz; 11.12 δ (1H) broad s.

EXAMPLE 1

(E)-N-Methyl-2-[3-(1,2,3,6-tetrahydro-1-methyl-4-pyridinyl)-1H-indol-5-yl]ethenesulphonamide A mixture of N-methylethenesulphonamide (460 g), Intermediate 1 (1 kg), palladium acetate (15.4 g), tri-o-tolylphosphine (315 g), triethylamine (960 mL) and celite (400 g) in DMF (5 L) was heated between 100°–108° under nitrogen for 2½ hr. The suspension was cooled to 5°, filtered and the filter cake washed with DMF (2 L). A portion (3.7 L) of the filtrate was stirred with water (250 mL) and cyclohexane (3.0 L) for 10 min. The phases were separated and the DMF layer re-extracted with cyclohexane (1×3.0 L, 1×1.5 L). The DMF solution was heated to 90° and water (2 L) added over 40 min. The mixture was cooled to 10° over 3 hr and then aged at 5° for 14 hr. The solid obtained was filtered off, washed with cold (10°) DMF/water (2:1) (2×500 mL) and dried in vacuo at 50° for 18 hr to afford a yellow powder (323.2 g, 60% of theory).

NMR:—2.33 δ (3H) s; 2.55 δ m; 2.57 δ broad s; 2.60 δ m (7H+DMSO-$d_5$); 3.10 δ (2H) m; 6.30 δ (1H) m; 7.00 δ (1H) broad resonance; 7.05 δ (1H) d, J=15.7 Hz; 7.45 δ (1H) d, J=8.4 Hz; 7.47 δ (1H) broad s; 7.51 δ (1H) d, J=15.7 Hz; 7.54 δ (1H) d of d, J=8.4 Hz, 1.6 Hz; 8.17 δ (1H) broad s; 11.38 δ (1H) broad s.

EXAMPLE 2

(E)-N-Methyl-2-[3-(1,2,3,6-tetrahydro-1-methyl-4-pyridinyl)-1H-indol-5-yl]ethenesulphonamide A mixture of N-methylethenesulphonamide (460 g), Intermediate 1 (1 kg), palladium acetate (15.4 g), tri-o-tolylphosphine (315 g), triethylamine (960 mL) and celite (400 g) in DMF (5 L) was heated between 100°–108° under nitrogen for 2½ hr. The suspension was cooled to 5°, filtered and the filter cake washed with DMF (2 L). Water (2.5 L) was added dropwise to a cold (4°) portion (3.7 L) of the filtrate. The suspension was cooled to 5°, aged for 45 min and filtered. The filter cake was washed with cold DMF/ water (7:5) (1 L) followed by cold IMS (1 L). The residue was slurried with ethyl acetate (2.76 L) at room temperature for 1 hr then filtered. The filter cake was washed with ethyl acetate (500 mL) and the collected solid dried overnight in vacuo at 45° (394.6 g, 69.3% of theory).

NMR:—2.32 δ (3H) s; 2.55 δ m; 2.56 δ d (J=4.8 Hz); 2.60 δ m (7H+DMSO-$d_5$); 3.09 δ (2H) m; 6.29 δ (1H) m; 6.99 δ (1H) q, J=4.8 Hz; 7.04 δ (1H) d, J=15.7 Hz; 7.44 δ (1H) d, J=8.4 Hz; 7.46 δ (1H) broad s; 7.51 δ (1H) d, J=15.7 Hz; 7.54 δ (1H) d of d, J=8.4 Hz, 1.6 Hz; 8.17 δ (1H) broad s; 11.38 δ (1H) broad s.

EXAMPLE 3

(E)-N-Methyl-2-[3-(1,2,3,6-tetrahydro-1-methyl-4-pyridinyl)-1H-indol-5-yl]ethenesulphonamide A mixture of N-methylethenesulphonamide (15.74 g), Intermediate 1 (30.02 g), palladium acetate (2.08 g), tri-o-tolylphosphine (7.21 g) and triethylamine (28.7 mL) in DMF (90 mL) was heated to 110°–115° for 4 hr. The mixture was filtered, whilst still hot, through hyflo. The filtrate was cooled to 0°–5° and ice cold water (300 ml) added over 30 mins. The mixture was stirred at 0°–5° for 1¼ hr then aged at 5° overnight. The resulting solid was collected by filtration washed with water (90 mL) and sucked dry for 20 min. The yellow solid was slurried with ethyl acetate (120 mL) at room temperature for 3 hr. The product was filtered off, washed with ethyl acetate (30 mL) and dried in vacuo at 55° overnight (28.06 g, 82% of theory).

NMR:—2.31 δ (3H) s; 2.55 δ m; 2.56 δ d (J=4.8 Hz); 2.60 δ m (7H+DMSO-$d_5$); 3.08 δ (2H) m; 6.28 δ (1H) m; 6.98 δ (1H) q, J=4.8 Hz; 7.03 δ (1H) d, J=15.7 Hz; 7.43 δ (1H) d, J=8.4 Hz; 7.45 δ (1H) d, J=1.9 Hz; 7.49 δ (1H) d, J=15.7 Hz; 7.52 δ (1 H) d of d, J=8.4 Hz, 1.6 Hz; 8.16 δ (1H) broad s; 11.38 δ (1H) broad s.

EXAMPLE 4

(E)-N-Methyl-2-[3-(1,2,3,6-tetrahydro-1-methyl-4-pyridinyl)-1H-indol-5-yl]ethene sulphonamide, hydrochloride A mixture of N-methylethenesulphonamide (320 g), Intermediate 1 (700 g), palladium acetate (10.5 g), tri-o-tolylphosphine (140 g), triethylamine (670 mL) and celite (280 g) in DMF (3.5 L) was heated at 85° for 4 hr. The mixture was filtered, whilst hot, and the filter cake washed with DMF (700 mL). The filtrate was cooled to 15°–20° and water (8.4 L) added dropwise. The mixture was aged at 8°, filtered, the product washed with water (2.1 L) then dried in vacuo overnight at 40°. The crude product was slurried in ethyl acetate (2.8 L) at 21° C. for 3 hr. The suspension was collected by filtration and washed with ethyl acetate (700 mL). The wet cake was suspended in DMF (2.1 L), cooled to 15° whereupon concentrated hydrochloric acid (210 mL) was added over 30 min at <25°. Ethyl acetate (1.4 L) was added dropwise over 30 mins. After a further 30 mins more ethyl acetate (5.6 L) was introduced over 1 hr. The product was filtered off, washed with ethyl acetate (1.4 L) followed by 2-propan-1-ol (700 mL) and dried in vacuo at 45° overnight (791.5 g, 89.5% of theory).

NMR:—2.55 δ (3H) d, J=5.0 Hz; 2.82 δ (2H) broad m; 2.89 δ (3H) s; 3.30 δ (1H) broad m; 3.58 δ (1H) broad m; 3.79 δ (1H) broad m; 3.98 δ (1H) broad m; 6.34 δ (1H) m; 7.05 δ (1H) q, J=5.0 Hz; 7.07 δ (1H) d, J=15.4 Hz; 7.47 δ (1H) d, J=8.5 Hz; 7.50 δ (1H) d, J=15.4 Hz; 7.58 δ (1H) d of d, J=8.5 Hz, 1.3 Hz; 7.62 δ (1H) d, J=2.6 Hz; 8.22 δ (1H) broad s; 10.7 δ (1H) broad resonance; 11.68 δ (1H) broad s.

EXAMPLE 5

(E)-N-Methyl-2-[3-(1,2,3,6-tetrahydro-1-methyl-4-pyridinyl)-1H-indol-5-yl]ethenesulphonamide A stirred mixture of Intermediate 2 (30.08 g), N-methylethenesulphonamide (14.84 g), palladium acetate (1.97 g), tri-o-tolylphosphine (6.81 g) and triethylamine (27 mL) in DMF (90 mL) was heated at 110°–115° for 4 hr. The hot (90°) mixture was filtered and the residue washed with DMF (30 mL). Water (300 mL) was added dropwise to the filtrate which was then cooled to 5° and aged for 30 mins. The suspension was filtered, washed with water (3×30 mL) and sucked dry for 1½ hr. The damp cake was slurried with ethyl acetate (120 mL) for 3 hr, filtered and the residue washed with ethyl acetate (30 mL). The product was dried in vacuo at 55° for 18 hr (27.52 g, 85% of theory).

NMR:—2.31 δ (3H) s; 2.55 δ m; 2.56 δ d, J=4.8 Hz; 2.60 δ m, (7H+DMSO-$d_5$); 3.08 δ (2H) m; 6.28 δ (1H) m; 6.98 δ (1H) q, J=4.8 Hz; 7.03 δ (1H) d, J=15.7 Hz; 7.43 δ (1H) d, J=8.4 Hz; 7.45 δ (1H) d, J=1.9 Hz; 7.50 δ (1H) d, J=15.7 Hz; 7.53 δ (1H) d of d, J=8.4 Hz, 1.6 Hz; 8.16 δ (1H) broad s; 11.39 δ (1H) broad s.

EXAMPLE 6

(E)-N-Methyl-2-[3-(1,2,3,6-tetrahydro-1-methyl-4-pyridinyl)-1H-indol-5-yl]ethenesulphonamide A mixture of N-methylethenesulphonamide (115 g), Intermediate 1 (250 g), palladium acetate (3.85 g), tri-o-tolylphosphine (77.5 g), triethylamine (240 mL) and celite (100 g) in DMF (1.25 L) was heated between 100°–110° under nitrogen for 2 h. The suspension was cooled to 20°, filtered and the filter cake washed with DMF (500 mL). The combined washings and filtrate were stirred with water (125 mL) and cyclohexane (1.5 L). The phases were separated and the DMF layer re-extracted with cyclohexane (1×1.5 L, 1×0.75 L). The DMF solution was treated with triethylamine (125 mL). Water (1.0 L) was added at ≦35° over 20 min. The suspension was cooled to 5° over 30 min and aged for 1.5 h. The solid was filtered off, washed with DMF/water (2:1) (2×250 mL) followed by water (125 mL) and dried in vacuo at 50° for 18 h to afford a yellow powder (194.3 g, 69% of theory).

NMR:—2.33 δ (3H) s; 2.5 δ m, 2.56 δ broad s, 2.61 δ m (7H+DMSO-$d_5$); 3.10 δ (2H) m; 6.30 δ (1H) m; 7.08 (1H) broad resonance, 7.04 δ (1H) d, J=15.7 Hz; 7.44 δ (1H) d, J=8.4 Hz; 7.46 δ (1H) s, 7.47 δ (1H) d, J=15.7 Hz; 7.54 δ (1H) d of d, J=8.4 Hz, 1.6 Hz; 8.18 δ (1H) broad s; 11.4 δ (1H) broad s.

EXAMPLE 7

(E)-N-Methyl-2-[3-(1,2,3,6-tetrahydro-1-methyl-4-pyridinyl)-1H-indol-5-yl]ethenesulphonamide A solution of Intermediate 1 (100 g) and N-methylethenesulphonamide (46 g) in DMF (300 mL) and 5N hydrochloric acid (70 mL) was added over 0.75 h to a stirred mixture of tri-o-tolylphosphine (31.3 g), palladium acetate (1.54 g), celite (40 g) and triethylamine (144 mL) in DMF (200 mL) at 100° under nitrogen. The reaction was stirred for a further 4h at 100°, cooled to ambient temperature, filtered and the filter cake washed with DMF (2×100 mL). The combined washings and filtrate were stirred with water (50 mL) and cyclohexane (600 mL). The phases were separated and the DMF layer re-extracted with cyclohexane (1×600 mL, 1×300 mL). The DMF solution was treated with triethylamine (48 mL). Water (400 mL) was added at ≦35° over 15 min, the suspension cooled to 5° and aged for 1 h. The solid was filtered off, washed with DMF/water (2:1) (2×100 mL) and dried in vacuo at 50° overnight to afford a yellow powder (76.9 g, 68% of theory).

NMR:—2.32 δ (3H) s; 2.55 δ m, 2.56 δ d (J=4.8 Hz), 2.60 δ m (7H+DMSO-$d_5$); 3.09 δ (2H) m; 6.28 δ (1H) m; 6.98 δ (1H) q, J=4.8 Hz; 7.03 δ (1H) d, J=15.7 Hz; 7.43 δ (1H) d, J=8.4 Hz; 7.45 δ (1H) s; 7.47 δ (1H) d, J=15.7 Hz; 7.53 δ (1H) d of d, J=8.4 Hz, 1.6 Hz; 8.17 δ (1H) broad s; 11.4 δ (1H) broad s.

EXAMPLE 8

(E)-N-Methyl-2-[3-(1,2,3,6-tetrahydro-1-methyl-4-pyridinyl)-1H-indol-5-yl]ethenesulphonamide A mixture of N-methylethenesulphonamide (43.08 g), Intermediate 2 (100 g), palladium acetate (1.45 g), tri-o-tolylphosphine (29.5 g), triethylamine (90 mL) and celite (40 g) in DMF (500 mL) was heated between 100°–110° under nitrogen for 4 h. The suspension was cooled to 20°, filtered and the filter cake washed with DMF (200 mL). The combined washings and filtrate were stirred with water (50 mL) and cyclohexane (600 mL). The phases were separated and the DMF layer re-extracted with cyclohexane (1×600 mL, 1×300 mL). The DMF solution was treated with triethylamine (45 mL). Water (400 mL) was added at ≦35° over 15 min, the suspension cooled to 5° over 1.5 h and aged for 1 h. The solid was filtered off, washed with DMF/water (2:1) (2×100 mL) followed by water (50 mL) and dried in vacuo at 50° for 18 h to afford a yellow powder (76.7 g, 67% of theory).

NMR:—2.33 δ (3H) s; 2.55 δ m, 2.57 δ s, 2.62 δ m, (7H+DMSO-$d_5$); 3.10 δ (2H) m; 6.30 δ (1H) m; 7.0 δ (1H) broad resonance, 7.05 δ (1H) d, J=15.7; 7.44 δ (1H) d, J=8.4 Hz; 7.46 δ (1H) s; 7.48 δ (1H) d, J=15.7 Hz; 7.55 δ (1H) d, J=8.4 Hz; 8.18 δ (1H) broad s; 11.4 δ (1H) broad s.

EXAMPLE 9

(E)-N-Methyl-2-[3-(1,2,3,6-tetrahydro-1-methyl-4-pyridinyl)-1H-indol-5-yl]ethenesulphonamide A mixture of Intermediate 3 (3.93 g), 1-methyl-4-piperidone (3.42 g) and potassium hydroxide (1.41 g) in IMS (35 mL) was heated under reflux for 17 h. The suspension was cooled to ambient temperature and filtered. The filter cake was washed with IMS (5 mL) followed by water (10 mL) and IMS (5 mL) again, then dried in vacuo. The crude product was triturated with water (30 mL), filtered, the filter cake washed with water (10 mL) and dried in vacuo at 50° to provide a pale yellow solid (2.30 g, 42% of theory).

NMR:—2.35 δ (3H) s; 2.57 δ (2H+DMSO-$d_5$) m; 2.60 δ (3H) s; 2.64 δ (2H) m; 3.12 (2H) m; 6.32 δ (1H) m; 7.07 δ (1H) d, J=15.7 Hz; 7.47 δ (1H) d, J=8.4 Hz; 7.49 δ (1H) s; 7.53 δ (1H) d, J=15.7 Hz; 7.56 δ (1H) d of d, J=8.4, 1.6 Hz; 8.20 δ (1H)s.

EXAMPLE 10

(E)-N-Methyl-2-[3-(1,2,3,6-tetrahydro-1-methyl-4-pyridinyl)-I H-indol-5-yl]ethene-sulphonamide A mixture of Intermediate 4 (1.0 g) and potassium hydroxide (90 mg) in IMS (15 mL) was heated under reflux for 20 hr. The solution was cooled to ambient temperature and the resulting yellow precipitate filtered off. The residue was washed with water (3'5 mL) followed by IMS (2×2 mL) and dried in vacuo to give a yellow powder (0.16 g, 17% of theory).

NMR:—2.35 δ (3H) s; 2.57 δ (2H+DMSO-$d_5$) m; 2.59 δ (3H) s; 2.64 δ (2H) m; 3.12 δ (2H) m; 6.22 δ (1H) m; 7.02 δ (1H) broad resonance; 7.07 δ (1H) d, J=15.7 Hz; 7.47 δ (1 H) d, J=8.4 Hz; 7.49 δ (1H) s; 7.50 δ (1 H) d, J=15.7 Hz; 7.57 δ (1H) d of d, J=8.4, 1.6 Hz; 8.20 δ (1H) s.

EXAMPLE 11

N-Methyl-3-(1-methyl-4-piperidinyl)-1H-indole-5-ethanesulphonamide, hydrochloride A mixture of (E)-N-methyl-2-[3-(1,2,3,6-tetrahydro-1-methyl-4-pyridinyl)-1H-indol-5-yl]ethenesulphonamide (10 kg) and 10% palladium oxide on charcoal (10 kg, 50% wet paste, added as two charges) in DMF (50 L), water (20 L) and 2N hydrochloric acid (15 L) was hydrogenated at atmospheric pressure over 18.5 hr. The catalyst was removed by filtration. The filter cake was washed with water (20 L). The filtrate was concentrated in vacuo to approximately 30 L and cooled to 20°. Ethyl acetate (70 L) was added over 1 hr and the resulting suspension cooled to 5° and aged for 30 min. The product was collected by filtration, washed with ethyl acetate (20 L) and dried in vacuo at 40°–50° overnight (9.34 kg, 81.6% of theory). A portion (2.0 kg) of the solid was recrystallised from hot water (6.0 L) and obtained as white crystals (1.40 kg, 70% of theory).

NMR:—2.1 δ (4H) m; 2.64 δ (3H) d, J=4.9 Hz; 2.78 δ (3H) s; 3.04 δ m; 3.11 δ broad m, (5H); 3.33 δ (2H) m; 3.47 δ (2H) m; 7.02 δ (2H) m; 7.14 δ (1H) broad s; 7.31 δ (1H) d, J=8.2 Hz; 7.60 δ (1H) broad s; 10.75 δ (1H) broad resonance; 10.9 δ (1H) broad s.

EXAMPLE 12

N-Methyl-3-(1-methyl-4-piperidinyl)-1H-indole-5-ethanesulphonamide, hydrochloride A mixture of (E)-N-methyl-2-[3-(1,2,3,6-tetrahydro-1-methyl-4-pyridinyl)-1H-indol-5-yl]ethenesulphonamide hydrochloride (500 g) and 10% palladium oxide on charcoal (50% wet paste, 700 g added as three charges) in DMF (3 L), water (3 L) and methanol (1.5 L) was hydrogenated at atmospheric pressure over 24 hr. The suspension was filtered and the filter cake washed with water (500 mL). The filtrate was concentrated to approximately 2 L by distillation in vacuo. Ethyl acetate (5 L) was added over 10 mins and the mixture cooled to 5°. The product was filtered off, washed with ethyl acetate (1 L) and dried in vacuo at 45° overnight (453 g, 90.1% of theory). Recrystallisation from hot water (1.36 L) afforded white crystals (324.0 g, 71.2% of theory).

NMR:—2.1 δ (4H) m; 2.64 δ (3H) d, J=4.9 Hz; 2.79 δ (3H) s; 3.04 δ m; 3.11 δ broad m, (5H); 3.33 δ (2H) m; 3.47 δ (2H) m; 7.02 δ (2H) m; 7.14 δ (1H) broad s; 7.31 δ (1H) d, J=8.2 Hz; 7.60 δ (1H) broad s; 10.65 δ (1H) broad resonance; 10.9 δ (1H) broad s.

EXAMPLE 13

N-Methyl-3-(1-methyl-4-piperidinyl)-1H-indole-5-ethanesulphonamide, hydrochloride A solution of (E)-N-methyl-2-[3-(1,2,3,6-tetrahydro-1-methyl-4-pyridinyl)-1H-indol-5-yl]ethenesulphonamide (25 g) in water (244.5 mL) containing methanesulphonic acid (5.5 mL) was hydrogenated at atmospheric pressure over 10% palladium oxide on charcoal (25 g, 50% wet paste, added as two charges). After 18 hr, hydrogen uptake ceased and the catalyst was removed by filtration. The filtrate was evaporated in vacuo to approximately 50 mL and concentrated hydrochloric acid (10 mL) added. Evaporation was continued and most of the water removed by azeotropic distillation with IMS (3×100 mL). The resulting suspension (~100 mL) was aged at 5° for 1.5 hr, filtered, and the residue washed with diisopropylether (2×100mL). The pale yellow solid (18.5 g, 66% of theory) was dried in vacuo at 55° for 20 h. Recrystallisation of a portion (15 g) from water gave off-white crystals (13.2 g, 88% of theory).

NMR:—2.1 δ (4H) m; 2.64 δ (3H) d, J=4.9 Hz; 2.79 δ (3H) s; 3.04 δ m; 3.11 δ broad m, (5H); 3.33 δ (2H) m; 3.47 δ (2H) m; 7.0 (2H) m; 7.13 (1H) broad s; 7.31 δ (1H) d, J=8.2 Hz; 7.60 δ (1H) broad s; 10.6 δ (1H) broad resonance; 10.9 δ (1H) broad s.

EXAMPLE 14

N-Methyl-3-(1-methyl-4-piperidinyl)-1H-indole-5-ethanesulphonamide, hydrochloride A mixture of (E)-N-methyl-2-[3-(1,2,3,6-tetrahydro-1-methyl-4-pyridinyl)-1H-indol-5-yl]-ethenesulphonamide (10 kg) and 10% palladium oxide on charcoal (10 kg, 50% wet paste, added as two charges) in DMF (50 L), water (35 L) and 2N hydrochloric acid (15.75 L) was hydrogenated at atmospheric pressure over 20.5 h. The catalyst was removed by filtration. The filter cake was washed with water (40 L). The filtrate was concentrated in vacuo to approximately 30 L and cooled to 18°. Ethyl acetate (70 L) was added over 1 h and the resulting suspension cooled to 5° and aged for 1 h. The product was collected by filtration, washed with ethyl acetate (20 L) and dried in vacuo at 40°–50° overnight (8.87 kg, 79.0% of theory). A portion (0.2 kg) of the solid was recrystallised from hot IMS/water (4:1) (1 L) and obtained as fine, off-white crystals (0.143 kg), 71.7% of theory).

NMR:—2.1 δ (4H) m; 2.64 δ (3H) d, J=4.9 Hz; 2.78 δ (3H) s; 3.04 δ m, 3.11 δ broad m, (5H); 3.33 δ (2H) m; 3.47 δ (2H) m; 7.0 (2H) m; 7.13 (1H) broad s; 7.31 δ (1H) d, J=8.2 Hz; 7.58 δ (1H) broad s; 10.5 (1H) broad resonance; 10.9 (1H) broads.

EXAMPLE 15

N-Methyl-3-(1-methyl-4-piperidinyl)-1H-indole-5-ethanesulphonamide, hydrochloride A mixture of (E)-N-methyl-2-[3-(1,2,3,6-tetrahydro-1-methyl-4-pyridinyl)-1H-indol-5-yl]ethenesulphonamide (8.6 kg) and 10% palladium oxide on charcoal (2.58 kg, 50% wet pastel in DMF (86 L) and 2 N hydrochloric acid (12.3 kg) was hydrogenated at atmospheric pressure over 21 h. The catalyst was removed by filtration. The filter cake was washed with DMF/water (1:1; 30 L). The combined washings and filtrate were then treated with decolourising charcoal (0.86 kg) at 75°–80° for 2 h. The suspension was filtered and the residue washed with DMF/water (2×30 L). The filtrates from two hydrogenations could be combined for work-up. Thus the combined solutions were treated with 2M hydrochloric acid (1.72 L) then concentrated in vacuo to approximately 52 L. Ethyl acetate (120 L) was added, the resulting suspension cooled to 3° and aged for 1 h. The product was collected by filtration, washed with ethyl acetate (2×26 L) and dried in vacuo at 40°–50° overnight (15.96 kg, 83% of theory). Recrystallisation from hot IMS/water (7:1; 206 L) gave fine, off-white crystals (13.02 kg, 84% of theory).

NMR:—2.1 δ (4H) m; 2.64 δ (3H) d, J=4.9 Hz; 2.78 δ (3H) s; 3.04 δ m, 3.11 δ broad m, (5H); 3.33 δ (2H) m; 3.47 δ (2H) m; 7.02 (2H) m; 7.12 (1H) broad s; 7.31 δ (1H) d, J=8.2 Hz; 7.62 δ (1H) broad s; 10.9 δ (2H) broad resonance.

EXAMPLE 16

N-Methyl-3-(1-methyl-4-piperidinyl)-1H-indole-5-ethanesulphonamide, hydrochloride A mixture of (E)-N-methyl-2-[3-(1,2,3,6-tetrahydro-1-methyl-4-pyridinyl)-1H-indol-5-yl]ethenesulphonamide (100 g) and 10% palladium oxide on charcoal (30 g, 50% wet pastel in DMF (1 L) and 2N hydrochloric acid (150 mL) was hydrogenated at atmospheric pressure over 48 h. The catalyst was removed by filtration. The filter cake was washed with DMF/water (1:1; 200 mL). The combined washings and filtrate were then treated with decolourising charcoal (10 g) at 75°–80° for 2 h. The suspension was filtered, the residue washed with DMF/water (1:1; 400 mL) and 2 M hydrochloric acid (10 mL) added. The filtrate was concentrated in vacuo to approximately 300 mL and cooled to 30°. Ethyl acetate (700 mL) was added over 30 min and the resulting suspension cooled to 0°–5° and aged for 30 min. The product was collected by vacuum filtration and washed with ethyl acetate (150 mL) follwed by IMS (2×150 mL). The IMS-damp cake was recrystallised from hot IMS/water (7:1) (1.315 L) and obtained as fine, off-white crystals (60.1 g, 54% of theory).

NMR:—2.1 δ (4H) m; 2.62 δ (3H) d, J=4.9Hz; 2.78 δ (3H) s; 3.02 δ m, 3.10 δ broad m, (5H); 3.31 δ (2H) m; 3.47 δ (2H) m; 6.98 (2H) m; 7.11 (1H) broad s; 7.29 δ (1H) d, J=8.2 Hz; 7.58 δ (1H) broad s; 10.5 (1H) broad resonance; 10.9 (1H) broad s.

We claim:

1. A process for the preparation of the compound of formula (I)

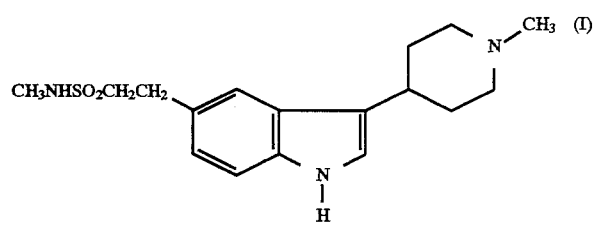

or a salt thereof which comprises reducing the compound of formula (II)

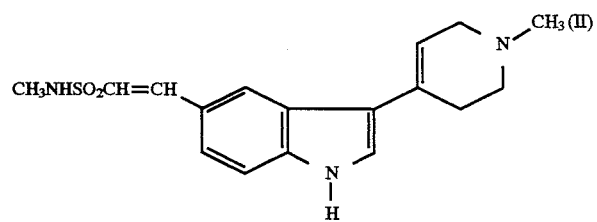

or a salt thereof.

2. A process as claimed in claim 1 wherein the reduction process is carried out in the presence of hydrogen and a noble metal catalyst.

3. A process as claimed in claim 2 wherein the noble metal catalyst is palladium, palladium oxide, Raney nickel, platinum, platinum oxide or rhodium, optionally supported on charcoal.

4. A process as claimed in claim 3 wherein the noble metal catalyst is palladium oxide on charcoal.

5. A process as claimed in claim 4 wherein the noble metal catalyst is 10% palladium oxide on charcoal.

6. A process as claimed in claim 5 wherein the palladium oxide is added to the reaction vessel in the form of a wet paste.

7. A process as claimed in claim 1 wherein the reduction process is carried out in the presence of hydrogen and a homogenous catalyst.

8. A process as claimed in claim 7 wherein the homogenous catalyst is tris (triphenylphosphine) rhodium chloride.

9. A process as claimed in claim 1 wherein the reduction process is carried out in a solvent comprising water or an alcohol, ether, ester or amide or a mixture thereof.

10. A process as claimed in claim 9 wherein the solvent is water, methanol, ethanol, dioxan, ethyl acetate, dimethylformamide or a mixture thereof.

11. A process as claimed in claim 1 wherein the reduction is carried out at a temperature of 10° to 50° C.

12. A process as claimed in claim 1 wherein the reduction process is carried out under conditions for catalytic hydrogen transfer.

13. A process as claimed in claim 12 wherein the reduction process is carried out using palladium in the presence of a hydrogen donor.

14. A process as claimed in claim 13 wherein the hydrogen donor is formic acid or a salt thereof.

15. N-methyl-2-[3-(1,2,3,6-tetrahydro-1-methyl-4-pyridinyl)-1H-indol-5-yl]ethenesulphonamide and salts thereof.

16. A process for the preparation of N-methyl-2-[3-(1,2,3,6-tetrahydro-1-methyl-4-pyridinyl)-1H-indol-5-yl) ethenesulphonamide and salts thereof which comprises:

condensing a compound of formula (III)

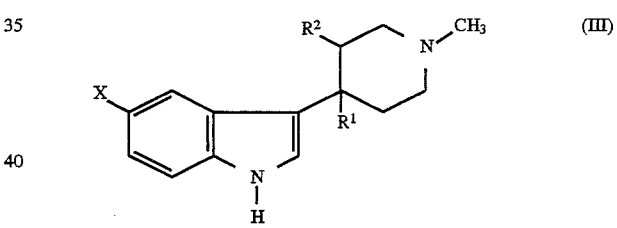

or a salt thereof, wherein $R^1$ is a hydroxy group and $R^2$ is hydrogen or $R^1$ and $R^2$ together form a double bond, X represents a leaving atom such as a halogen atom, for example a bromine atom, or a leaving group, for example a triflate ($CF_3SO_3$) group, with an N-methyl vinylsulphonamide of formula (IV)

where Z is hydrogen or an amino protecting group, and optionally, if necessary and/or desired, deprotecting a protected derivative so obtained.

* * * * *